(12) United States Patent
Hansen et al.

(10) Patent No.: US 7,955,288 B2
(45) Date of Patent: Jun. 7, 2011

(54) GELATINE-BASED MATERIALS AS SWABS

(75) Inventors: John E. Hansen, Søborg (DK); Nikolaj Haulrik, Copenhagen K (DK)

(73) Assignee: Ferrosan Medical Devices A/S (DK)

( * ) Notice: Subject to any disclaimer, the term of this patent is extended or adjusted under 35 U.S.C. 154(b) by 17 days.

(21) Appl. No.: 10/538,918

(22) PCT Filed: Dec. 11, 2003

(86) PCT No.: PCT/DK03/00855
§ 371 (c)(1),
(2), (4) Date: Dec. 13, 2005

(87) PCT Pub. No.: WO2004/053051
PCT Pub. Date: Jun. 24, 2004

(65) Prior Publication Data
US 2006/0115805 A1 Jun. 1, 2006

Related U.S. Application Data

(60) Provisional application No. 60/432,232, filed on Dec. 11, 2002.

(30) Foreign Application Priority Data

Dec. 11, 2002 (DK) .................................. 2002 01896

(51) Int. Cl.
*A61M 35/00* (2006.01)
(52) U.S. Cl. .......................................................... 604/1
(58) Field of Classification Search .................. 604/1–3
See application file for complete search history.

(56) References Cited

U.S. PATENT DOCUMENTS

| | | | |
|---|---|---|---|
| 2,465,357 A | 3/1949 | Correll | |
| 2,465,860 A | 3/1949 | Fleischmann | |
| 2,558,395 A | 6/1951 | Studer | |
| 3,224,434 A | 12/1965 | Molomut et al. | |
| 3,678,933 A | 7/1972 | Moore et al. | |
| 3,815,580 A | 6/1974 | Oster | |
| 3,869,539 A | 3/1975 | Kring et al. | |
| 3,930,052 A | 12/1975 | De Brou et al. | |
| 4,098,728 A | 7/1978 | Rosenblatt | |
| 4,265,233 A | 5/1981 | Sugitachi et al. | |
| 4,280,954 A | 7/1981 | Yannas et al. | |
| 4,320,201 A | 3/1982 | Berg et al. | |
| 4,492,305 A | 1/1985 | Avery | |
| 4,515,637 A | 5/1985 | Cioca | |
| 4,522,302 A | 6/1985 | Paikoff | |
| 4,559,304 A | 12/1985 | Kasai et al. | |
| 4,655,211 A | 4/1987 | Sakamoto et al. | |
| 4,696,812 A | 9/1987 | Silbering et al. | |
| 4,735,616 A | 4/1988 | Eibl et al. | |
| 4,749,689 A | 6/1988 | Miyata et al. | |
| 4,851,521 A | 7/1989 | della Valle et al. | |
| 4,861,714 A | 8/1989 | Dean, Jr. et al. | |
| 4,863,856 A | 9/1989 | Dean, Jr. et al. | |
| 4,891,359 A | 1/1990 | Saferstein et al. | |
| 4,982,769 A | 1/1991 | Fournier et al. | |
| 4,997,753 A | 3/1991 | Dean et al. | |
| 5,024,841 A | 6/1991 | Chu et al. | |
| 5,037,740 A | 8/1991 | Tanaka et al. | |
| 5,112,750 A | 5/1992 | Tanaka et al. | |
| 5,149,540 A | 9/1992 | Kunihiro et al. | |
| 5,180,583 A | 1/1993 | Hedner | |
| 5,356,883 A | 10/1994 | Kuo et al. | |
| 5,387,208 A | 2/1995 | Ashton et al. | |
| 5,394,886 A | 3/1995 | Nabai et al. | |
| 5,399,361 A | 3/1995 | Song et al. | |
| 5,401,511 A | 3/1995 | Margalit | |
| 5,443,481 A | 8/1995 | Lee | |
| 5,456,693 A | 10/1995 | Conston et al. | |
| 5,462,860 A | 10/1995 | Mach | |
| 5,503,848 A | 4/1996 | Perbellini et al. | |
| 5,512,301 A | 4/1996 | Song et al. | |
| 5,595,735 A | 1/1997 | Saferstein et al. | |
| 5,643,596 A | 7/1997 | Pruss et al. | |
| 5,645,849 A | 7/1997 | Pruss et al. | |
| 5,660,854 A | 8/1997 | Haynes et al. | |
| 5,669,934 A | 9/1997 | Sawyer | |
| 5,690,675 A | 11/1997 | Sawyer et al. | |

(Continued)

FOREIGN PATENT DOCUMENTS

BG 0051589 A1 7/1993

(Continued)

OTHER PUBLICATIONS

Kelly, M.J. et al, "The value of an operative wound swab sent in transport medium in the prediction of later clinical wound infection: A controlled clinical and bacteriological evaluation", Brit.J. Surgery, 65:2, Abstract only.* Google search result showing disclosure of handled Gelfoam swab in the body of the Kelly publication.*
English Derwent Abstract of Ranjane reference.*
Stuart Transport medium information sheet.*
Gelfoam RTM product information sheet.*
Y.S. Choi et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J. of Materials Sci.: Mat. in Med., vol. 12 (2001).*
Kelly, "The value of an operative wound swab sent in transport medium in the prediction of later clinical wound infection: a controlled clinical and bacteriological evaluation," Brit. J. Surgery, vol. 65, ~X). 81-88, 1978.*
Gelfoam (TM) Trademark description, http://www.uspto.gov., 1947.*
Kelly, "The value of an operative wound swab sent in transport medium in the prediction of later clinical wound infection: a controlled clinical and bacteriological evaluation," Brit. J. Surgery, vol. 65, -X). 81-88, 1978.*

(Continued)

*Primary Examiner* — Melanie J Hand
(74) *Attorney, Agent, or Firm* — Jonathan D. Ball; King & Spalding LLP

(57) ABSTRACT

A swab comprising gelatine or collagen has been found to have a remarkably high recovery of microorganisms. Furthermore, the samples, such as microorganisms, spores, nucleotides and other biologically or biochemically relevant compounds can be fully recovered from the collagen-or gelatine-comprising swab. The invention thus provides a method and swab which has a high recovery of a target from a sample and furthermore a second high recovery when transferring from the swab to a medium for analysis.

20 Claims, No Drawings

U.S. PATENT DOCUMENTS

| | | |
|---|---|---|
| 5,690,954 A | 11/1997 | Illum |
| 5,700,476 A * | 12/1997 | Rosenthal et al. ............ 424/426 |
| 5,712,161 A | 1/1998 | Koezuka |
| 5,723,308 A | 3/1998 | Mach et al. |
| 5,743,312 A | 4/1998 | Pfeifer et al. |
| 5,749,895 A | 5/1998 | Sawyer et al. |
| 5,791,352 A | 8/1998 | Reich et al. |
| 5,795,330 A | 8/1998 | Tofighi et al. |
| 5,798,091 A | 8/1998 | Trevino et al. |
| 5,804,203 A * | 9/1998 | Hahn et al. .................... 424/401 |
| 5,823,671 A | 10/1998 | Mitchell et al. |
| 5,824,015 A | 10/1998 | Sawyer |
| 5,883,078 A | 3/1999 | Seelich et al. |
| 5,890,610 A | 4/1999 | Jansen et al. |
| 5,895,412 A | 4/1999 | Tucker |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,986,168 A | 11/1999 | Noishiki et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,162,241 A | 12/2000 | Coury et al. |
| 6,168,788 B1 | 1/2001 | Wortham |
| 6,218,176 B1 * | 4/2001 | Berthold et al. ............ 435/287.9 |
| 6,261,596 B1 | 7/2001 | Li et al. |
| 6,280,727 B1 | 8/2001 | Prior et al. |
| 6,283,933 B1 * | 9/2001 | D'Alessio et al. ................. 604/3 |
| 6,300,128 B1 | 10/2001 | Morota et al. |
| 6,303,323 B1 * | 10/2001 | Laskey et al. ................. 435/7.23 |
| 6,312,725 B1 | 11/2001 | Wallace et al. |
| 6,334,865 B1 | 1/2002 | Redmond et al. |
| 6,364,519 B1 | 4/2002 | Hughes et al. |
| 6,387,413 B1 | 5/2002 | Miyata et al. |
| 6,454,787 B1 | 9/2002 | Maddalo et al. |
| 6,458,380 B1 | 10/2002 | Leaderman |
| 6,461,325 B1 | 10/2002 | Delmotte et al. |
| 6,495,127 B1 | 12/2002 | Wallace et al. |
| 6,548,081 B2 | 4/2003 | Sadozai et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 7,052,713 B2 | 5/2006 | Stimmeder |
| 7,125,860 B1 | 10/2006 | Renier et al. |
| 7,427,607 B2 | 9/2008 | Suzuki |
| 7,435,425 B2 | 10/2008 | Qian et al. |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt |
| 2002/0012982 A1 * | 1/2002 | Blakesley et al. ............. 435/183 |
| 2002/0015724 A1 | 2/2002 | Yang et al. |
| 2002/0019062 A1 * | 2/2002 | Lea et al. ...................... 436/518 |
| 2002/0025921 A1 | 2/2002 | Petito et al. |
| 2002/0026215 A1 | 2/2002 | Redmond et al. |
| 2002/0039594 A1 | 4/2002 | Unger |
| 2002/0042378 A1 | 4/2002 | Reich et al. |
| 2002/0061842 A1 | 5/2002 | Mansour |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0181659 A1 | 9/2003 | Naranda et al. |
| 2003/0232746 A1 | 12/2003 | Lamberti et al. |
| 2004/0076647 A1 | 4/2004 | Biering |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0214277 A1 | 9/2005 | Schaufler |
| 2005/0218541 A1 | 10/2005 | Peng et al. |
| 2005/0245905 A1 | 11/2005 | Schmidt et al. |
| 2006/0002890 A1 | 1/2006 | Hersel et al. |
| 2006/0068013 A1 | 3/2006 | DiTizio et al. |
| 2006/0159733 A1 | 7/2006 | Pendharkar et al. |
| 2006/0189516 A1 | 8/2006 | Yang et al. |
| 2006/0193846 A1 | 8/2006 | Stimmeder |
| 2007/0009578 A1 | 1/2007 | Moller et al. |
| 2007/0025955 A1 | 2/2007 | Lowinger et al. |
| 2007/0264301 A1 | 11/2007 | Cleek et al. |
| 2007/0264302 A1 | 11/2007 | Cleek et al. |
| 2008/0095830 A1 | 4/2008 | Van Holten |
| 2008/0311172 A1 | 12/2008 | Schapira et al. |
| 2009/0087569 A1 | 4/2009 | Fan et al. |

FOREIGN PATENT DOCUMENTS

| | | |
|---|---|---|
| BG | 0099900 A | 3/1997 |
| DE | 3146841 | 6/1983 |
| DE | 4119140 | 12/1992 |
| DE | 4407875 | 9/1995 |
| EP | 0 156 649 A2 | 10/1985 |
| EP | 0156649 | 10/1985 |
| EP | 0341745 B | 11/1989 |
| EP | 0365705 | 5/1990 |
| EP | 0 372 966 | 6/1990 |
| EP | 0372966 | 11/1990 |
| EP | 0395758 | 11/1990 |
| EP | 0478827 | 4/1992 |
| EP | 0 341 745 | 12/1994 |
| EP | 0 702 081 A2 | 3/1996 |
| EP | 0702081 | 3/1996 |
| EP | 0737467 | 10/1996 |
| EP | 0773740 | 11/1999 |
| EP | 1005874 B | 6/2000 |
| EP | 1 022 031 | 7/2000 |
| EP | 1022031 A | 7/2000 |
| EP | 1044693 | 10/2000 |
| EP | 1053758 | 11/2000 |
| EP | 1140235 | 10/2001 |
| EP | 1 174 463 | 1/2002 |
| EP | 1174463 A | 1/2002 |
| EP | 1258256 | 11/2002 |
| EP | 0790823 | 7/2003 |
| EP | 0891193 | 8/2003 |
| EP | 1 005 874 | 5/2005 |
| EP | 1 095 064 | 6/2005 |
| EP | 1095064 | 6/2005 |
| EP | 1095064 B | 6/2005 |
| EP | 1059957 | 8/2007 |
| FR | 2 679 772 | 5/1993 |
| FR | 2679772 | 5/1993 |
| FR | 2 759 980 | 8/1998 |
| FR | 2759980 | 8/1998 |
| GB | 697603 | 9/1949 |

| | | |
|---|---|---|
| GB | 648619 | 1/1951 |
| GB | 697603 | 9/1953 |
| GB | 697603 A * | 9/1953 |
| GB | 1 584 080 | 2/1981 |
| GB | 1584080 | 2/1981 |
| GB | 2266239 | 10/1993 |
| GB | 2 393 120 | 3/2004 |
| GB | 2393120 A | 3/2004 |
| GB | 2414021 | 11/2005 |
| JP | 60214728 | 10/1985 |
| JP | 62070318 | 3/1987 |
| JP | 62 221357 | 9/1987 |
| JP | 62-221357 | 9/1987 |
| JP | 01-130519 | 5/1989 |
| JP | 01 130519 | 5/1989 |
| JP | 06254148 | 9/1994 |
| JP | 10-507666 | 7/1998 |
| JP | 2002-513308 | 5/2002 |
| JP | 2004-002271 | 1/2004 |
| WO | WO 89/02730 | 4/1989 |
| WO | WO 90/13320 | 11/1990 |
| WO | WO 9013320 | 11/1990 |
| WO | WO 93/06802 | 4/1993 |
| WO | WO 9306802 | 4/1993 |
| WO | WO 9306855 | 4/1993 |
| WO | WO 9310768 | 6/1993 |
| WO | WO 9321908 | 11/1993 |
| WO | WO 9408552 | 4/1994 |
| WO | WO 94/17840 | 8/1994 |
| WO | WO 9417840 | 8/1994 |
| WO | WO 9512371 | 5/1995 |
| WO | WO 9525748 | 9/1995 |
| WO | WO 95/31955 | 11/1995 |
| WO | WO 9531955 | 11/1995 |
| WO | WO 96/07472 | 3/1996 |
| WO | WO 9607472 | 3/1996 |
| WO | WO 9616643 | 6/1996 |
| WO | WO 9640033 | 12/1996 |
| WO | WO 9717023 | 5/1997 |
| WO | WO 9717024 | 5/1997 |
| WO | WO 9717025 | 5/1997 |
| WO | WO 9729792 | 8/1997 |
| WO | WO 9737694 | 10/1997 |
| WO | WO 9808550 | 3/1998 |
| WO | WO 9831403 | 7/1998 |
| WO | WO 9836784 | 8/1998 |
| WO | WO 98/43092 A1 | 10/1998 |
| WO | WO 9843092 | 10/1998 |
| WO | WO 9844963 | 10/1998 |
| WO | WO 9851282 | 11/1998 |
| WO | WO 9904828 | 2/1999 |
| WO | WO 99/12032 A1 | 3/1999 |
| WO | WO 9912032 | 3/1999 |
| WO | WO 9938606 | 8/1999 |
| WO | WO 99/44901 | 9/1999 |
| WO | WO 9944901 | 9/1999 |
| WO | WO 9945938 | 9/1999 |
| WO | WO 0009018 | 2/2000 |
| WO | WO 00/18301 | 4/2000 |
| WO | WO 0018301 | 4/2000 |
| WO | WO 2005/044285 | 5/2000 |
| WO | WO 0027327 | 5/2000 |
| WO | WO 0061201 | 10/2000 |
| WO | WO 0074742 | 12/2000 |
| WO | WO 0076533 | 12/2000 |
| WO | WO 0113956 | 3/2001 |
| WO | WO 01/28603 | 4/2001 |
| WO | WO 0128603 | 4/2001 |
| WO | WO 01/34206 A2 | 5/2001 |
| WO | WO 0134206 | 5/2001 |
| WO | WO 0154735 | 8/2001 |
| WO | WO 0166161 | 9/2001 |
| WO | WO 0197826 | 12/2001 |
| WO | WO 02/18450 | 3/2002 |
| WO | WO 0218450 | 3/2002 |
| WO | WO 0222059 | 3/2002 |
| WO | WO 0240068 | 5/2002 |
| WO | WO 02058749 | 8/2002 |
| WO | WO 03/007845 | 1/2003 |
| WO | WO 03007845 | 1/2003 |
| WO | WO 03/055531 | 7/2003 |
| WO | WO 03055531 | 7/2003 |
| WO | WO 03/070110 | 8/2003 |
| WO | WO 03094983 | 11/2003 |
| WO | WO 2004/028583 | 4/2004 |
| WO | WO 2004/035629 | 4/2004 |
| WO | WO 2004028404 | 4/2004 |
| WO | WO 2004028423 | 4/2004 |
| WO | WO 2004028583 | 4/2004 |
| WO | WO 2004029095 | 4/2004 |
| WO | WO 2004030711 | 4/2004 |
| WO | WO 2004035629 | 4/2004 |
| WO | WO2004053051 | 6/2004 |
| WO | WO 2004108035 | 12/2004 |
| WO | WO 2005000265 | 1/2005 |
| WO | WO 2005009225 | 2/2005 |
| WO | WO 2005041811 | 5/2005 |
| WO | WO 2005044285 | 5/2005 |
| WO | WO 2005062889 | 7/2005 |
| WO | WO 2006034568 | 4/2006 |
| WO | WO 2006063758 | 6/2006 |
| WO | WO 2007133699 | 11/2007 |
| WO | WO 2008051758 | 5/2008 |
| WO | WO 2008090555 | 7/2008 |
| WO | WO 2009109963 | 9/2009 |

OTHER PUBLICATIONS

Luengo et al., "Prevention of Peritoneal Adhesions by the combined use of Spongostan and 32% Dextran 70: an experimental study in pigs", Fertility and Sterility, vol. 29, No. 4, p. 447-450, 1978.

Raftery, A., "Absorbable Haemostatic Materials and Intraperitoneal adhesion formation", Br. J. Surg., vol. 67, p. 57-58, 1980.

Sanfilippo et al., "Comparison of Avitene, topical thrombin and Gelfoam, as sole hemostatic agent in tuboplastics", Fetility and Sterility, vol. 33, No. 3, p. 311-316, 1980.

Soules et al., "The prevention of postoperative pelvic adhesions: An animal study comparing barrier methods with Dextran 70", Am. J. Obstet. Gynecol., vol. 143, p. 829-834, 1982.

Laurent et al., "Hyaluronic Acid reduces connective tissue formation in middle ears filled with absorbable gelatin sponge: an experimental study", Am. J. Otolaryngol, vol. 7, p. 181-186, 1986.

Maxson et al., "Efficacy of a modified oxidized cellulose fabric in the prevention of adhesion formation", Gynecol. Obstet. Invest., vol. 26, p. 160-165, 1988.

Hill et al., "Use of Microfibrillar collagen hemostat (Avitenet) and thrombin to achieve hemostasts after median sternotomy", J. Thorac Cardiovasc. Surg., vol. 108, p. 1151-1152, 1994.

Hill-West et al., "Efficacy of a resorbable hydrogel barrier, oxidized regenerated cellulose and hyaluronic acid in the prevention of ovarian adhesions in a rabbit model", Fertility and Sterility, vol. 62, No. 3, p. 630-634, 1994.

Larsson et al. "Surgicel®—An absorbable heostatic material—In prevention of peritoneal adhesion in rats", Acta Chir. Scand., vol. 26, p. 375-378, 1978.

Shushan et al., "Hyaluronic acid for preventing experimental postoperative intraperitoneal adhesions", Journal of Reproductive Medicine, vol. 39, No. 5, p. 398-402, 1994.

West et al., "Efficacyof adhesion barriers: resorable hydrogel, oxidized regenerated cellulose and hyaluronic acid", The Journal of Reproductive Medicine, vol. 41, No. 3, p. 149-154, 1996.

Kocak et al., "Reduction of adhesion formation with cross-linked hyaluronic acid after peritoneal surgery in rats" Fertility and Sterility, vol. 72, No. 5, p. 873-878, 1999.

Reijnen et al., "Prevention of Intra-Abdominal Abscesses and adhesions using a hyaluronic acid solution in a rat peritonitis model", Arch Surg., vol. 134, p. 997-1001, 1999.

Oz et al., "Controlled clinical trial of a novel heostatic agent in cardiac surgery", Ann. Thorac. Surg., vol. 69, p. 1376-1382, 2000.

De Iaco et al., "Efficacy of a Hyaluronan Derivative gel in postsurgical adhesion prevention in the presence of inadequate hemostasis", Surgery, vol. 130, No. 1, p. 60-64, 2001.

Li et al., "Evaluation of Esterified Hyaluronic Acid as middle ear-packing material", Arch Otolaryngol Head Neck Surg., vol. 127, p. 534-539, 2001.

Ellegala et al., "Use of FloSeal Hemostatic Sealant in Transsphenoidal Pituitary Surgery: technical note", Neurosurgery, vol. 51, No. 2, p. 513-516, 2002.
FloSeal Matrix Hemosealant, Instructions of Use, (Accessed online Aug. 17, 2005 at http://www.ctsnet.org/file/vendors/931/pdf/140.pdf).
Soules et al, Am. J. Obstet. Gynecl., vol. 143, p. 829-834, 1982, "The prevention of postoperative pelvic adhesions: An animal study comparing barrier methods with Dextran 70".
De Iaco, et al., Surgery, vol. 130, p. 60-64, 2001, "Efficacy of a Hyaluronan Derivative gel in postsurgical adhesion prevention in the presence of inadequate hemostasis".
Sakurabayashi etal., Gastroenterological Endoscopy 30(10) Oct. 1988. Clinical evaluation of new hemostatic agent for hemostasis from biopsy wounds in the liver.
Spence et al., Cancer Feb. 1975;35(2):326-341. Cerebellar capillary hemangioblastoma: its histogenesis studied by organ culture and electron microscopy.
Changez et al, Biomaterials, 2005, vol. 26, No. 14, p. 2095-2104, "Efficacy of antibiotics-loaded interpenetrating network (IPNs) hydrogel based on poly (acrylic acid) and gelatin for treatment of experimental osteomyelitis: in vivo study".
Quintavalla et al., Biomaterials Jan. 2002;23(1):109-119. Fluorescently labeled mesenchymal stem cells (MSC)maintain multilineage potential and can be detected following implantation into cartilage defects.
Hill-West, et al., Fertility and Sterility, vol. 62, No. 3, p. 630-634, "Efficacy of a resorbable hydrogel barrier, oxidized regenerated cellulose and hyaluronic acid in the prevention of ovarian adhesions in a rabbit model".
Shushan, et al., Journal of Reproductive Medicine, vol. 39, p. 398-402, 1994, "Hyaluronic acid for preventing experimental postoperative intraperitoneal adhesions".
Yuesong et al. Intern. des Services de San. des Forces Armees, Sep. 1999, vol. 72, No. 7-9, p. 194-196, "Design and experimental study of a slow-release antibiotic membrane implant in surgery wound".
Raftery, Br. J. Surg., vol. 67, p. 57-58, 1980, "Absorbable Haemostatic materials and intraperitoneal adhesion formation".
Oz et al, Ann Thorac Surg 2000, vol. 69, p. 1376-1382, 2000, "Controlled clinical trial of a novel hemostatic agent in cardiac surgery".
Choi YS et al, J Biomed Mater Res 1999; 48(5), p. 631-639, "Studies on gelatin-containing artificial skin: II. Preparation and characterization of cross-linked gelatin-hyaluronate sponge".
Larsson, et al., Acta Chir. Scand., vol. 26, p. 375-378, 1978, "Surgicel—An absorbable hemostatic material—In prevention of peritoneal adhesions in rats".
Dembo, M. A et al, Lech. Prep. Krovi. Tkanei, p. 139-40, 1974, "Antiseptic hemostatic preparations, their properties and study".
Laurent et al, Am. J. Otolaryngol, vol. 7, p. 181-186, 1986, "Hyaluronic acid reduces connective tissue formation in middle ears filled with absorbable gelatin sponge: an experimental study".
Kocak, et al., Fertility and Sterility, vol. 72, No. 5, p. 873-878, Nov. 1999, "Reduction of adhesion formation with cross-linked hyaluronic acid after peritoneal surgery in rats".
Wachol-Drewek et al, Biomaterials 17, p. 1733-1738, 1996, "Comparative Investigation of drug delivery of collagen implants saturated in antibiotic solutions and a sponge containing gentamicin".
Wiesenthal et al, The Journal of Otolaryngology, 1999, vol. 28, No. 5, p. 260-265, "New method for packing the external auditory canal, middle ear space, and mastoid cavities after otologic surgery".
Ellegala et al, Neurosurgery, Aug. 2002, vol. 51, p. 513-516, "Use of FloSeal Hemostatic Sealant in Transsphenoidal Pituitary surgery: technical note".
Drognitz et al, Indection Germany (Munich), 2006, 34 (1), p. 29-34, "Release of vancomycin and teicoplanin from a plasticized and resorbable gelatin sponge: in vitro investigation of a new antibiotic delivery system with glycopeptides".
"FloSeal Matrix Hemosealant. Instructions for use". Accessed online Aug. 17, 2005 at http://www.ctsnet.org/file/vendors/931/pdf/140.pdf.
Luengo, et al., Fertility and Sterility, vol. 29, No. 4, Apr. 1978, "Prevention of peritoneal adhesions by the combined use of Spongostan and 32% Dextran 70: an experimental study in pigs".
Maxson et al, Gynecol. Obestet. Invest., vol. 26, p. 160-165, 1988, "Efficacy of a modified oxidized cellulose fabric in the prevention of adhesion formation".

Hong et al, Biomaterials, 2001, 22 (20), p. 2777-2783, "Study on gelatin-containing artificial skin IV: a comparative study on the effect of antibiotic and EGF on cell proliferation during epidermal healing".
Van Der Salm T.J. et al, J. of Thoracic and Cardiovascular Surgery, 1989, vol. 98, No. 4, p. 618-622, "Reduction of sternal infection by application of topical vancomycin".
West, et al., The Journal of reproductive medicine, vol. 41, p. 149-154, 1996, "Efficacy of adhesion barriers, resorbable hydrogel, oxidized regenerated cellulose and hyaluronic acid".
Sanfilippo et al, Fertility and sterility, vol. 33, No. 3, p. 311-316, Mar. 1980, "Comparison of avitene, topical thrombin and Gelfoam, as sole hemostatic agent in tuboplasties".
Hae-Won et al, J. of Biomedical Materials Research, 2005, 74B (2), p. 686-698, "Porous scaffolds of gelatin-hydroxyapatite nanocomposites obtained by biometic approach: Characterization and antibiotic drug release".
Li, et al., Arch Otolaryngol Head Neck Surg., vol. 127, p. 534-539, May 2001, "Evaluation of Esterified Hyaluronic Acid as middle ear-packing material".
Reijnen, et al., Arch Surg., vol. 134, p. 997-1001, Sep. 1999, "Prevention of Intra-Abdominal Abscesses and adhesions using a hyaluronic acid solution in a rat peritonitis model".
Hill et al, J. Thorac Cardiovasc Surg 1994, vol. 108, p. 1151-1152, "Use of microfibrillar collagen hemostat (Avitenet) and thrombin to achieve hemostats after median sternotomy".
Y.S. Choi et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J. of Materials Sci.: Mat. in Med., vol. 12 (2001)
Kelly, "The value of an operative wound swab sent in transport medium in the prediction of later clinical wound infection: a controlled clinical and bacteriological evaluation," Brit. J. Surgery, vol. 65, pp. 81-88, 1978.
Gelfoam® RIM product information sheet, Pfizer, Jul. 2007.
International Preliminary Examination Report for International Application No. PCT/DK03/00855 dated Jun. 6, 2005.
M.G. Cascone et al.; "Collagen and hyaluronic acid based polymeric blends as drug delivery systems for the release of physiological concentrations of growth hormone." Journal of Materials science: Materials in Medicine; No. 5, 1994; pp. 770-774.
Min et al. "Molecular Weight Changes of Sodium Hyaluronate Powder and Solution by Heat treatment," Matrix Biology Institute, Proceedings of Hyaluronan, Oct. 11-16, 2003.
Branski et al., "Mucosal Wound Healing in a Rabbit Model of Subglottic Stenosis," Arch Otolaryngol Head Neck Surg, vol. 131, Feb. 2005, p. 153-157.
Cantor et al., "Gelfoam® and Thrombin in treatment of massive gastroduodenal hemorrhage—A preliminary report," American Journal of Surgery, Dec. 1950.
Purdy et al., "Microfibrillar collagen model of canine cerebral infarction," Stroks, vol. 20 No. 10, Oct. 1989, p. 1361-1367.
Santomaso at al., "Powder flowability and density ratios: the impact of granules packing," Chemical Engineering Science 58 (2003) 2857-2874.
Swann, "Studies on hyaluronic acid—I. The preparation and properties of rooster comb hyaluronic acid," Biochemica et biophysica acta, 156 (1968) p. 17-30.
Spence et al., "Cerebellar Capillary Hemangioblastoma: Its Histogenesis Sudied by organ Culture and Electron Microscopy", Cerebellar Hemangioblastoma in Vitro,I Cancer, vol. 35, No. 2, p. 326-341, 1975.
Solar Biologicals Inc., "Solar-Cult Sampling Products Pre-Moistened Cellulose Sponge Sampling Systems", www.solarbiologicals.com/samp-sys.htm, 2002.
Ouintavalla et al., "Fluorescently Labeled Mesenchymal Stem Cells (MSCs) Maintain Multilineage Potential and can be Detected Following Implantation in Articular Cartilage Defects", Biomaterials, vol. 23, p. 109-119, 2002.
Written Opinion, PCT/DK03/00855, Feb. 28, 2005.
Communication Relating to the Results of the Partial International Search, PCT/DK03/00855.

* cited by examiner

GELATINE-BASED MATERIALS AS SWABS

CROSS-REFERENCE TO RELATED APPLICATIONS

This patent application is a U.S. national stage application of International Application No. PCT/DK2003/000855, filed 11 Dec. 2003, which claims priority of Denmark Patent Application No. PA 2002 01896, filed Dec. 11, 2002. The International Application also claims the benefit of U.S. Provisional Patent Application No. 60/432,232, filed Dec. 11, 2002. All of the above applications are incorporated herein by reference in their entireties.

FIELD OF THE INVENTION

A gelatine or collagen-based material is used in the collection of targets such as microbiological cells, mammalian cells, nucleotides and other chemical and biological molecules from an array of collection media.

BACKGROUND OF THE INVENTION

Gelatine-based sponges have been used as haemostatic agents in surgical procedures.

Dean Jr. (U.S. Pat. Nos. 4,997,753; 4,863,856 and 4,861,714) discloses the use of weighted collagen microsponges for immobilising bioactive materials.

EP 0 702 081 discloses a matrix for tissue culturing comprising two kinds of sponges.

U.S. Pat. No. 5,462, 860 discloses a culture medium for rapid growth and detection of microbes.

Conventional methods of sampling an area for a target area comprise the use of cotton swabs. Sample recovery from the surface is limited due to the low recovery from the surface area to the swab and then low transfer from the swab to a culturing medium. The level of recovery of micro-organisms from surfaces is critical when complying with USP/NF guidelines and EU-GMP guidelines. The present invention addresses this problem and provides for a dramatically improved device for sampling an area.

SUMMARY OF THE INVENTION

A gelatine-based sponge has been found to be useful in the collection of a variety of materials, such as microbes and mammalian cells, but also mammalian tissue and various molecules, including nucleotides, from an array of collection media. The sponge can be used for instance for sampling and culturing purposes. The present inventors have surprisingly found that the sponge has a dramatically higher recovery level of the sampled material than conventional methods. Moreover, the target material bound to the sponge can be transferred from the sponge to another medium by an array of methods.

A first object of the invention relates to a device comprising a device for sampling or collecting comprising i) a swab comprising gelatine or collagen; and ii) a support fixed to said swab.

The device or the gelatine-based sponge may be used for an array of applications related to the high recovery of targets from the sponge. Accordingly, a further object of the invention relates to the use of a gelatine-based sponge for collection of a target from a collection medium comprising making contact between the gelatine-based sponge and the medium. Furthermore, an object of the invention relates to a method of lowering the amount of a target in a sample area comprising making contact between a gelatine-based sponge and at least a portion of said sample area, such that the target adheres to the sponge. An important and further utilisation of the surprising properties of the sponge relate to a method of qualitatively or quantitatively sampling an area for content of a target comprising the use of a gelatine-based sponge and the steps of i) wet sampling using the gelatine-based sponge; and/or ii) dry-sampling using the gelatine-based sponge. A similarly important aspect of the invention relates to a method for culturing micro-organisms or mammalian cells comprising adhering the cells to a gelatine-based sponge and culturing the cells in a growth medium.

The invention provides a swab which has a high recovery of a target from a sample and furthermore a second high recovery when transferring from the swab to a medium for analysis.

DESCRIPTION OF THE INVENTION

In the present context, a target refers to any species which binds to the gelatine-based sponge of the invention. A collection medium refers to any medium from which said targets may be collected. The term "transfer medium" is intended to mean a medium to which the collected target is transferred.

In the present context, the term "recovery" is intended to mean the overall recovery yield of a target from a collection medium to transfer medium. Thus, recovery comprises i) the collection yield of a target to the collagen-based sponge of the present invention, as well as ii) the transfer yield from the collagen-based sponge to a transfer medium.

A first transfer medium is, in the present context, considered to be a medium used in the collection of a target from the sponge. Suitable examples of a first transfer medium include an enzymatic solution, or a suitable washing agent to mechanically or chemically remove the target from the sponge into the medium, such as a liquid medium. A second transfer medium is considered to be represented by a second medium into which the first medium or the sample from the first medium, which includes the collected target, is transferred.

In the present context, a micro-organism is considered to be any organism selected from the group consisting of bacteria, bacterial spores, archea, yeast and fungi.

A dispersion agent is, in the present context, considered to be any liquid agent into which targets may be dispersed following collection.

A neutral diluent is considered to be a liquid which is neutral in the context of the assay process, i.e. it does not interfere with the diagnostic assay being performed. In this context, therefore, a neutral diluent is not necessarily, but can be, a diluent with neutral pH. Water, aqueous buffer solutions are suitable examples of neutral diluents.

Ringer's solution refers to an aqueous solution comprising distilled water and sodium chloride, potassium chloride, and calcium chloride at roughly the same concentrations as their occurrence in body fluids.

A "semi-solid surface" is a surface which is not strictly solid in nature, such as mammalian tissue or any other natural and/or synthetic tissue. Suitable examples of semi-solid surfaces are mammalian skin or other surfaces covered by connective tissue, such as surfaces of mammalian organs.

In the present context, a "detergent" can be any natural or synthetic, organic or inorganic, compound or a mixture of compound used for cleaning purposes, such as for the removal of impurities or contaminants from a surface.

The term "handle" in the present context is to be considered to relate to any device that can be used for gripping, and should not be construed to be limited to devices specially designed to act as a handle. By way of an example, a stick attached to the gelatine-based sponge of the invention can thus be used to handle the sponge, and is therefore considered to represent a handle. Moreover, a tweezer or tong, which only temporarily connect to the sponge, is to be considered a handle.

A swab is in the present context considered to be any material used for applying or removing material from an area or a surface. Swabbing refers to the method of applying or removing material from an area or surface using said swabs.

The present invention relates to gelatine-based sponges and their properties with respect to binding of targets, such as micro-organisms and mammalian cells, as well as molecular species such as nucleotides, which are suitable for binding to the gelatine-based sponges. The binding properties of the aforementioned targets are useful for the collection of said targets from various media. Once the target is collected, it may be optionally be released from the sponge by mechanical, enzymatic, or chemical processes.

The target is typically selected from the group consisting of a virus, a micro-organism, a mammalian cell and an organic molecule. The organic molecule is selected from the group consisting of a nucleotide, a nucleic acid, protein or a detergent. The nucleotide is a purine- or a pyrimidine-containing nucleotide, preferably ATP. The micro-organism is selected from the group consisting of bacteria, archea, bacterial spores, yeast and fungi.

The mammalian cell may be selected from the group consisting of cells from blood plasma, leukocytes, erythrocytes, thrombocytes, but also other mammalian cells such as skin cells or any other type of mammalian cells that may be useful to collect for various diagnostic and/or cleaning purposes.

The high recovery rate, resulting from the high collection yield of a target to the swab of the present invention, and/or the subsequent high transfer yield from the swab to a transfer medium requires, according to the present invention, i) a swab comprising gelatine or collagen. The swab is typically fixed onto a handle or support In a particularly interesting embodiment of the invention, the swab may be selected from the group consisting of a gelatine-based sponge, collagen-based sponge, microfibrillar gelatine or microfibrillar collagen. Preferably, the swab is a gelatine-based sponge or collagen-based sponge, more preferably a gelatine-based sponge. The gelatine-based sponge or collagen-based sponge material is preferentially comprised of at least 50% gelatine or collagen, respectively, such as at least 60%, such as at least 70%, typically at least 75%, preferably at least 80%, more preferably at least 85%, such as at least 90%, suitably at least 95%, most preferably selected from at least 96%, 97%, 98%, 99% gelatine or collagen, respectively, based on the dried weight of the sponge.

In a most preferred embodiment, the swab is a gelatine sponge or a collagen sponge, more preferably a gelatine sponge. That is to say that the swab itself is a sponge, typically comprising at least 95%, most preferably selected from at least 96%, 97%, 98%, 99% gelatine or collagen, respectively, based on the dried weight of the sponge.

The gelatine-based sponge or collagen-based sponge are characterised by their physical properties, which in particular may be described by the gelatine or collagen composition, pore size, reconfirmation rate, water absorption and digestibility of the sponge.

Without being bound to a particular theory, the pore size of the sponge is considered to influence, at least In part, the ability of the sponge is collect and transfer the targets of the invention. Moreover, the pore size influences the density of the sponge, and also has an effect on its physical characteristics, such as reconfirmation rates and water absorption.

Without being bound to a particular theory, the high recovery may be, in part, due an appropriate degree of roughness Imparted by the surface of the swab, allow collection of the samples onto the surface of the swab of the invention. Furthermore, without being bound by a particular theory, the physical properties imparted by the chemical nature of the collagen or gelatine comprised in the swab may also, in part, by an adhesion mechanism, contribute to the high recovery rate.

Without being bound by a particular theory, it is believed that appropriate pore size imparts, in part, an improvement to the high initial recovery. The gelatine or collagen in the gelatine-based sponge, collagen-based sponge, microfibrillar gelatine and micorfibrallar collagen will form or have pores with an average pore size of about 10 nm to about 2 mm. Without being bound by any one theory, particularly in a non-anhydrous environment, high recovery from the collection medium may be imparted by a form of capillary action into the swab. For the collection or sampling of viruses, at least 10% of the pores may have a pore size of less 1000 nm, such as less than 800 nm, such as less than 500 nm, such as less than 400 nm. For the collection or sampling of bacteria, at least 10% of the pores may have a pore size of less than 100 µm, such as less than 80 µm, such as less than 50 µm, such as less than 10 µm. For the collection or sampling of fungi or red blood cells, at least 10% of the pores may have a pore size of less than 1000 µm, such as less than 800 µm, such as less than 500 µm, such as less than 100 µm, such as less than 50 µm. It is within the meets and bounds of the skilled person to tailor the gelatine or collagen to a desired pore size and within the meets and bounds of the skilled person to select the pore size in accordance with the target.

In a typical embodiment of the invention, the gelatine or collagen of the gelatine-based or collagen-based sponge is of porcine origin. It is envisaged that the invention may be adapted to include gelatine with other origins, such as gelatine of bovine, or any other mammal, including marine mammal, fish or crayfish or vegetable origin, and including gelatine of any other origin, such as of gelatine of organic origin, or synthetic or semi-synthetic origin.

Reconfirmation rates represent a measure of the elasticity of the gelatine-based or collagen-based sponge. In one embodiment of the invention, the gelatine-based sponge has a reconfirmation rate of no more than 10 seconds, and typically no more than 5 seconds. However, it is envisaged that sponges based on gelatine from various sources will have a wider range of reconfirmation. The reconfirmation rate is typically determined by a method based on the rate at which the sponge regains its original size and shape, as described in Example 1.

The gelatine-based sponge of the invention typically has a water absorption capacity which is in the range of at least 30 g/g and more typically at least 40 g/g, as determined in Example 3. It is however envisaged that the water absorption capacity of sponges based on gelatine from various sources may be in a wider range of at least 5 g/g, such as at least 10 g/g or at least 20 g/g. The determination of water absorption is typically performed according to USP standards.

In a further embodiment of the invention, the swab is a natural or synthetic material, such as an absorbent material comprising gelatine particles or collagen particles, preferably gelatine particles. The natural or synthetic absorbent material is essentially any material which within it or upon its surface can contain loosely bound or fixed, gelatine or cartilage particles. The gelatine or collagen particles may be entrapped by the loose or tight weave or matrix of the material or by a adhesive substance. Within this embodiment, the particles may have a particle size in the range of about 1 μm to about 2 mm, typically from about 5 μm to about 1 mm, such as from about 5 μm to about 0.5 mm, more typically about 5 μm to about 0.25 mm, preferably about 10 μm to about 0.25 mm, such as about 10 μm to about 0.1 mm.

The swab has a content of gelatine particles or collagen particles, preferably gelatine particles, constituting from 1-95% wt/wt based upon the combined dry weight of the swab and the particles, such as 2-90%, typically 5-90%. As the skilled person will appreciate, the weight content will depend upon the nature of the natural or synthetic material.

The swab is intended for use on an array of surfaces and other collection medium. Depending upon the use and collection medium, whether it be industrial machinery, walls, table tops, air vents to use in equipment in conventional or micro-scale laboratories, the size of the swab will vary. Typically, the swab is of the size in the range of about 1 cm×1 cm to about 15 cm×15 cm. It may be of any shape, depending on its use. Particular interesting is the use of collagen-based sponges or gelatine-based sponges since these are highly compressible and can be forced or squeezed into all crevices and holes.

A further aspect of the invention is directed to a kit comprising i) a swab comprising gelatine or collagen; and ii) an agent selected from the group consisting of a neutral diluent, an anti-microbial agent and a dispersion agent. The swab may be as described above. The agent selected from the group consisting of a neutral diluent, an anti-microbial agent and a dispersion agent is present in order to assist in the collection or sampling of the target.

A further aspect of the invention relates to the use of a device or kit as desribed herein for collection of a target from a collection medium comprising making contact between the swab and the target.

The inventors have found that the gelatine-based sponge binds micro-organisms tightly but reversibly. Thus, the swab may be used for sampling for the presence of micro-organisms from a sample, such as from a surface. In such an embodiment, the micro-organism can be transferred from the swab by the methods of the invention. The thus collected micro-organisms may optionally be furthermore cultivated, which may find uses for specific purposes such as detailed characterization of said micro-organism. Alternatively, the swab may be used for quantitative removal of micro-organisms from a sample, such as a surface. In such an embodiment, anti-microbial or disinfecting agents may optionally be suitably incorporated into the swab.

It is furthermore envisaged that the swab may be adapted for use In collecting other types of cells in addition to micro-organisms, such as mammalian cells. Such an embodiment may be realised by, e.g. collection from mammalian surfaces, such as from mammalian skin or the surface of any mammalian organ. Furthermore, the swab may be adapted for internal use, such as during surgical operations on a mammal, and may in such embodiments be used to collect targets from wounds or from internal organs of a mammal, as well as surgical equipment and specialised furniture, walls or floors in a health clinic or a hospital, such as in surgical rooms, or in any other facility used to conduct or perform surgical procedures.

The inventors have furthermore found that the gelatine-based sponge binds certain molecules, such as purine- or pyrimidine-based nucleotides or nucleic acids, preferentially ATP, in a reversible fashion. This finding may find a useful application in that bacterial numbers have been estimated in foods by measuring the amount of bacterial adenosine triphosphate (ATP). It is envisaged that the swab may more generally be adapted to collect a variety of molecular species, and thus the swab may find general use for collection of certain molecules.

In one embodiment, such molecules are purine- or pyrimidine-based nucleotides, such as ATP. In another embodiment, such molecules are nucleic acids. In yet another embodiment, the molecules are detergents, which may conveniently be collected from a sample, such as a surface. In this context, detergents can be any natural or synthetic, organic or inorganic, compound or a mixture of compound used for cleaning purposes, such as for the removal of impurities or contaminants from a surface.

Furthermore, the swab may be adapted to collect a mixture of micro-organisms, mammalian cells and/or molecules simultaneously from a sample. In certain embodiments, it may be useful to configure the gelatine-based sponge such that one particular type of target is collected.

The desirable property of the swab in that it is capable of adhering to a target such as micro-organisms or mammalian cells as well as molecular species, especially organic molecules such as nucleotides, make a variety of useful applications possible.

In a suitable embodiment of the invention, the swab is adapted so that it comes into contact with or is attached to a support. The purpose of a support can be that of providing a way of handling the swab without touching the sponge material itself, and thus avoiding contamination. This may be especially useful for embodiments in which the sponge is ideally pre-sterilized, i.e. in embodiments for the collection or analysis of micro-organisms or mammalian cells. A support may also facilitate the use of the swab, and allow convenient collection of targets from various samples. A support can furthermore be invaluable for the collection of targets from samples that may be difficult to reach or for other applications in which the swab is difficult to manipulate without a support.

The support may be made of any suitable material for the particular use such as wood, natural or synthetic polymeric material, including plastics and rubber materials, or any other organic or inorganic material suitable for the particular embodiment.

The support may be of a wide variety, such as conveniently in the form of a handle. The handle may be short, such as in the range of about 1 cm to about 30 cm, such as about 3 cm to about 20 cm, preferably about 5 cm to about 15 cm. For certain applications, a handle may suitably be considerably larger, such as in the range of about 30 cm to several meters in length. The handle may be of any shape convenient for the particular embodiment, but is typically elongated, optionally bent, with the gelatine-based sponge attached at one end of the handle, while the other end of the handle is used for gripping and otherwise applying the gelatine-based sponge In one suitable embodiment, in which the swab is attached to a support in the form of a handle, the gelatine-based sponge has an oval or otherwise elongated shaped sponge positioned at the end of a stick, which serves the function of a handle. In another embodiment, the sponge is attached to a solid support, such as a circular or rectangular support, which in turn is positioned on the end of a handle or stick. It should however be appreciated that the swab may be adapted to be attached to a support in the form of a stick or handle in multiple different embodiments, suitably adapted for any given use of the gelatine-based sponge.

In another embodiment, the support is optionally in the form of a coating. The coating may be comprised of any suitable material, e.g. polymeric material or plastic material, or any other material suitably used to provide a coating. In a suitable embodiment, the coating is applied to one side of a swab of the invention which has been adapted to be in a flat shape.

In yet another embodiment, the support is a solid material which has a suitably adapted shape, such as the shape of a disc, cube, sphere or a block. In such embodiments, the gelatine-based sponge is preferably attached to one side of the support, but may be attached to several or all surfaces of the support in preferred embodiments.

An embodiment in which the swab is of a cubical shape may be particularly useful is an embodiment for collection of liquid samples or collection from surfaces comprising a liquid coating. In such embodiments, the swab may suitably be attached to a support, which may optionally be in the shape of a handle, or suitably attached to a stick or a handle.

It should be appreciated, that due to the nature of the swab material, it may be adapted to a shape for any particular use. Thus, the dimensions and shape of the embodiments wherein the invention is realised by mounting the swab onto a support, will be adjusted as ideally suited for their uses.

The swab may be attached to the support by any conventional method known to those skilled in the art. The nature of such embodiments will depend on the particular shape of the embodiment and its intended use.

It is furthermore envisaged that the support may be in the form of a porous container, such as a crucible or otherwise suitable material shaped such that it encloses the swab while allowing liquid and targets to pass through the enclosing material. In such embodiments, the encased gelatine-based sponge can be used to collect samples from a liquid. Such collection may suitably be performed by immersing the encased sponge into the liquid medium, thus allowing targets in the medium to come into contact with and bind to the gelatine-based sponge.

In embodiments of the swab in which it is adapted to collect gaseous targets, it is preferably adapted such that the surface area and/or pore size of the sponge is maximized. Such embodiments may be realized in accordance with any of the embodiments disclosed above, since the nature of binding of gaseous targets follows the same principles as that of targets in a liquid medium. Gaseous targets may be any molecular species, which is gaseous at the temperature applied during collection, or is a liquid or a solid compound which has a vapour pressure high enough so that the target may be collected. A gaseous target is in this context considered to include targets which are solid in nature, including micro-organisms and mammalian cells, but either are trapped in liquid droplets or microdroplets or form particles that may be carried by gases, such as ambient atmosphere.

In a further aspect of the invention, gelatine powder or collagen powder may be applied directly to a sample for collection of targets, such as when the sample is or found within a liquid or fluid. The gelatine powder may in such embodiments be recovered by filtration, centrifugation or by other means known in the art.

The gelatine powder may also be enclosed by a crucible or other suitable material shaped such that it encloses the powder, while allowing liquid and targets to pass through the enclosing material. Such embodiments may in particular be useful for collection from liquid media. In yet another embodiment, the enclosing material is permeable to gaseous targets, and the collection of targets is realised by placing the encased powdered gelatine material in an environment containing said gaseous targets.

Methods used for collecting targets from a surface using the swab of the present invention include techniques such as swab techniques and count-tact techniques. Swab techniques involve in principle a mechanical swiping or swabbing of a target, such as a surface, and are well known to those skilled in the art. Count-tact techniques involve the use of a specially designed instrument, as disclosed in Example 6.

In one embodiment of the invention, the gelatine-based sponge, optionally attached to a support, is used to collect targets from a sample. The target may be selected from the group comprising a micro-organism, mammalian cell, but may also be mammalian tissue, or alternatively a molecular species, such as a nucleic acid or a purine- or pyrimidine-based nucleotide, preferentially ATP. The micro-organism may be selected from the group consisting of bacteria, archea, bacterial spores, yeast, or fungus. The mammalian cell can be of any mammalian cell type, but may in particular be selected from the group consisting of cells from blood plasma, leukocytes, erythrocytes, thrombocytes, epithelial cells, skin cells or any other mammalian cell type that may be useful to collect for various diagnostic and/or cleaning purposes.

In a preferred embodiment, targets are collected from a surface using a combination of wet-sampling and dry-sampling. In this context, wet-sampling is considered to comprise the use of a gelatine-based sponge of the invention, which optionally has been attached to a support and has been pre-wetted with a suitable neutral diluent or a dispersing agent. Such a diluent or dispersion agent serves the purpose of facilitating the recovery of the targets from the surface, while not interfering with the assay. The diluent and dispersion agents may be any suitable aqueous solution, optionally including salts or other agents not toxic or otherwise chemically or biologically harmful for the targets to be collected, such as saline, saline peptone, buffered saline peptone, Ringer solution and an organic or inorganic buffer, optionally containing inorganic salts. The diluent or dispersion agent may also optionally contain growth media suitable for the micro-organism or mammalian cell type being collected, for assays directed towards such targets. The sponge may also optionally be presterilized. Collection of targets is realized by swiping the surface with at least one such pre-wetted sponge, followed by swiping of said surface with at least one dry gelatine-based sponge. The purpose of the dry swiping is to recover as much as possible of remaining liquid and target from the surface.

Collection of targets may, in other embodiments, be realised by wet-sampling or dry-sampling alone. The choice of method to use will vary depending on the sample type to be assayed and the target type to be collected.

Targets, including micro-organisms, mammalian cells and/or molecules collected in the swab are typically transferred from the swab. Transfer of such collected targets comprises removing or unbinding such targets from the sponge into a suitable medium. In a preferred embodiment, this is accomplished by placing the gelatine-based sponge in a medium comprising a solution capable of digesting the gelatine-based sponge. Digestion of the sponge may be realized by chemical and/or enzymatic methods, preferably using enzymes such as proteases, more preferably using proteases such as alcalase or pepsin. Digestion by chemical means may comprise using mineral or carboxylic acids, or bases, in appropriate concentration not to denature the target. In one embodiment, digestion comprises using a mixture of at least one enzyme, and may optionally include a mineral acid or a base, and optionally inorganic salts as well as organic or inorganic buffering agents. The temperature suitable for recovery of targets from the sponge will be highly dependent on the method used. In embodiments wherein transfer is realised using enzymes, the experimental temperature will be adjusted so as to maximise the efficiency of digestion for the particular enzyme in the context of the composition of the digestion medium employed.

In general, transfer of targets from the gelatine-based sponge of the invention may be realised by any technique known in the art which releases said target from the sponge. Thus, this may occur by changes in conditions such as pH or temperature, or by adding salts, chaotrophic agents or organic solvents. Transfer from the sponge may also optionally include mechanical action, such as that generated by rubbing or shaking the sponge, or by other mechanical means facilitating the unbinding of targets from the sponge. Transfer from the sponge may furthermore be realized by washing of a target from the gelatine-based sponge.

It is envisaged that preferred embodiments of the invention will include digestion methods for releasing micro-organisms and/or mammalian cells from the sponge, since micro-organisms and mammalian cells are in general sensitive to changes in conditions. However, there may be exceptions to this, and in particular it is envisaged that for certain applications it will be useful to use changes in experimental conditions for recovery of certain microorgansisms or mammalian cells, in particular extremophiles, which are organisms adapted to withstand harsh conditions of pH, salt, temperature and/or organic solvents. Recovery of bound molecules to the sponge may be accomplished by any of the aforementioned techniques, depending on any given embodiment of the invention and the type of molecule bound.

Micro-organisms or mammalian cells recovered from the gelatine-based sponge may optionally be further isolated using membrane filtration, wherein the membrane filter has properties such that it allows solvent and small molecules to pass through the filter, while whole cells and micro-organisms do not. In a typical embodiment, such a filter has a pore size of less than 1 µm, such as less than 0.8 µm, such as less than 0.6 µm, more typically less than 0.45 µm, such as less than 0.2 µm.

In another embodiment of the invention, the gelatine-based sponge is used to disinfect a sample, such as a surface. In such an embodiment, the combined action of the sponge, which acts to remove targets, in this case micro-organisms and/or mammalian cells, from a sample, and optionally an antimicrobial or a disinfecting agent, facilitates the effective removal of said micro-organisms or mammalian cells from the sample, thus rendering it sterile. The sponge is in such embodiments preferably sterilised by methods known in the art, such as by heat and/or radiation, and optionally pretreated with an anti-microbial or disinfecting agent. Such an agent is preferably a liquid, such as an alcohol, an aqueous solution comprising an alcohol or other liquid agent which kills micro-organisms or mammalian cells, but may be any compound which facilitates the sterilization procedure. Embodiments for sterilization of samples may be realized by packaging individual gelatine-based sponges, optionally attached to a support and optionally pretreated with a sterilizing agent, individually into sealed packages, which are ideally intended for single use.

In another embodiment of the invention, viable micro-organisms or mammalian cells which have been trapped on the gelatine-based sponge can be cultured. Culturing in general requires contacting a micro-organism or mammalian cell and a suitable growth medium. The growth medium may in the form of a liquid; alternatively, it is in the form of solid agar. The growth medium is comprised of components well known to those skilled in the art. Realisation of said culturing can be accomplished by conventional techniques, including:

1. Contacting the gelatine-based sponge, optionally attached to a support, and a liquid or a solid growth medium. In one such embodiment, a suitably shaped gelatine-based sponge positioned at the end of a stick is used to collect targets from a surface, and subsequently allowed to come into contact with a growth medium, such that micro-organisms or mammalian cells collected by the sponge are transferred to the growth medium.
2. Injecting a liquid growth medium, optionally agar-containing, into the gelatine sponge, thus providing conditions for in situ growth of the bound micro-organisms or mammalian cells in the gelatine-based sponge.
3. Transferring the gelatine-based sponge to a container with liquid growth medium, thus allowing for culturing of the entire population of bound micro-organisms or mammalian cells in said growth medium.

It should be appreciated that the culturing of collected micro-organisms or mammalian cells may be preceded by a step in which bound cells have been unbound or by other means released into a medium. In such embodiments, said medium is considered to be a first transfer medium. The medium can be any liquid suitable for the application, such as a neutral diluent, a dispersion agent, or a growth medium. Unbinding of bound micro-organisms or mammalian cells may be realized by any of the methods described herein, including enzymatic and/or chemical digestion of the gelatine-based sponge, and may include mechanical transfer into said first transfer medium. The thus unbound micro-organisms or mammalian cells are subsequently transferred to a second transfer medium, which is ideally comprised of a liquid or solid growth medium. The transfer to a second transfer medium may be partial, i.e. a sample from said first growth medium is transferred to said second transfer medium. Alternatively, the transfer is complete, i.e. the entire volume of the first transfer medium is transferred Into the second tranfer medium.

Culturing of micro-organisms or mammalian cells collected by the gelatine-based sponge of the invention may in particular be useful for further characterization or production of the collected micro-organisms or mammalian cells. Preferred embodiments of the gelatine-based sponge may, for example, be used for qualitative determination of the microbiological and/or mammalian cell composition of a target population collected from a sample. In such embodiments, the sample may, for example, be a surface in a food production line, such as meat or fish processing lines, or from other surfaces such as floors, walls, or equipment used in such processing lines. Alternatively, the sample may be a surface from equipment, specialized furniture or walls or floors from a health clinic or hospitals, such as surgical rooms. The sample may also be collected from an open wound, from the surface of an internal organ or it may be comprised of any mammalian tissue. In principle, however, the gelatine-based sponge may be adapted for collecting and culturing targets from any sample, from which it is useful to determine the microbiological and/or mammalian cell content.

In one embodiment, the collection medium is a solid surface from which targets may be collected. In a second embodiment, the medium is a liquid, from which targets may also be collected. In such an embodiment, the high water absorption capacity of the gelatine-based sponge is a useful characteristic, as it allows collection of large volumes of water. The liquid medium may be located on a surface, for example in cavities on the surface. The sponge therefore can be adapted to be useful for the collection of targets from a wide variety of sources, such as manufacturing devices in food manufacturing, processing plants for meat and/or fish products, medical devices, as well as the management and cleaning of wounds, such as surgical wounds.

It is furthermore envisaged that the gelatine-based sponge may be adapted for use in collecting targets from other types of samples of liquid and/or gaseous nature.

In principle, collection may be from a solid surface irrespective of the material from which the surface is comprised, such as natural or synthetic surfaces, of organic or inorganic material. Furthermore, targets may be collected from semi-solid surfaces, such as mammalian surfaces and mammalian tissue, including mammalian skin and the surface of mammalian organs.

EXAMPLES

The following methods and examples illustrate how the gelatine-based sponge of the present invention may for specific uses be adapted for the collection and recovery of bacterial spores from a stainless steel surface. Recovery yields, i.e. the overall yields for the transfer from the surface to the sponge and the subsequent transfer from the sponge to a medium, are very high which is an illustration of the usefulness of the gelatine-based sponge for the collection and transfer of targets from a sample, such as a stainless steel surface.

These methods and examples should however only be understood as examples of useful embodiments of the present invention, and in no way limiting for its adaptation for other use.

Example 1

Determination of Reconfirmation time of Gelatine-Based Sponges

The purpose of this method is to determine the reconfirmation rate of a gelatine-based sponge. The method comprises soaking the sponge, and subsequently squeezing it. The appearance of the native shape of the sponge is monitored as a function of time, and the time that lapses until the sponge has reached its native shape is termed the reconfirmation time.

The method comprises the following steps:
1. Cut a suitable piece of absorbable gelatine-based sponge, approximately 1×1 cm, and thoroughly soak it in water at room temperature.
2. Remove the sample from the water, and squeeze it until it is flat and no more air bubbles or drops of water can be pressed out.
3. Place the sample in a beaker filled with water at room temperature and measure the time (in seconds) until the sample has gained its former size and shape.
4. Repeat the test twice and report the result as the average of three determinations.

Example 2

Determination of Digestability of Gelatine-Based Sponges using Pepsin

Purpose: To Determine the Digestion Time of a Gelatine-Based Sponge by Enzymatic Means using Pepsin.
Reagents used in the Method:
Milli-Q-water
Pepsin(1:3000)
Hydrochloric acid dilute, Ph. Eur.
Pepsin solution 1%:

Accurately weigh 20.0 g of pepsin and dissolve in 100 ml hydrochloric acid dilute, using a 2000 ml volumetric flask. Add water to volume and mix.

Apparatus:
Metallic filament basket, 6 cm ø, 1 mm openings.
Thermostated water bath
Method:
1. Transfer 100 ml of the pepsin solution (1%) to a 250 ml beaker. Add a magnet and place the beaker in a water bath, previously warmed to 37° C. on a magnetic stirrer.
2. Cut off a piece of absorbable gelatine sponge weighing 50±5 mg, and place it in a beaker of water. Knead gently between the fingers until the gelatine sponge is thoroughly wet, and until all the air has been removed, taking care not to break the tissue.
3. Lift from water and squeeze gently to remove any excess water.
4. Place the wetted sample in a metallic filament basket in the beaker, and start the timer.
5. Watch until the piece of absorbable gelatine sponge is entirely dissolved, stop the timer, and note the consumption of time.
6. Repeat the test twice—a total of three times and calculate average.

Alternative Method for a Gelatine Powder
1. Transfer 100 ml of the pepsin solution (1%) to a 250 ml beaker. Add a magnet and place the beaker in a water bath, previously warmed to 37° C. on a magnetic stirrer.
2. Prepare a sample weighing out approximately 50 mg±5 mg.
3. Place the sample directly in the beaker.
4. Watch until the absorbable gelatine powder is entirely dissolved, stop the timer, and note the consumption of time.
5. Repeat the test twice—a total of three times and calculate average of three determinations.

Example 3

Determination of Water Absorption of Gelatine-Based Sponges

Purpose: To determine the amount of water that a gelatine-based sponge can absorb. The sponge is expected to absorb several times its own weight of water on a weight to weight basis.

Method: According to USP Method "Absorable Gelatine Sponge: Water absorption". A total of 6 determinations on 6 different pieces of gelatine-based sponge are performed.

Example 4

Size Measurements of a Celatine-Based Sponge

Purpose: The dimensions weight, height, length, width, centre hole and diameter of the gelatine sponge are measured on 6 samples; one series of measurements Is performed for each of the 6 samples. The average of the 6 measurements is reported. The density is calculated.

Apparatus: A caliper, Mitutoyo 500-Series or similar.
A ruler specifically made for the determination of length and width of absorbable gelatine sponge film.
Balance, Mettler AK 160 or a balance with similar accuracy.

Method and Calculations: The wanted measurements are made with a caliper or a ruler. The average of 6 measurements performed on 6 samples is reported (in mm).

The weight of the sponge is measured. The average of 6 measurements performed on 6 samples is reported (in 0.001 g). The density of the absorbable gelatine sponge, anal is calculated in the following way:

$$\frac{4*\text{weight}}{\pi*\text{length}*(D^2-d^2)} = \text{density, mg/mm}^3$$

where
D=diameter of the sponge.
d=diameter of the pore in the sponge.

Example 5

Sampling Protocol from a Stainless Steel Surface using Wet Sampling and Dry Sampling Purpose: To sample a stainless steel surface using a combination of wet sampling and dry sampling.
Materials:
A gelatine-based sponge.
Saltwater-peptone solution
Alcalase solution
A stainless steel surface with a 24 cm² contact area.
Stomacher bags
Method:
1. Swab the stainless steel sheets horizontally from left to right covering the 24 cm² contact area using a gelatine sponge swab moistened with saltwater-peptone solution.
2. Swap the stainless steel sheets vertically from top to bottom covering the 24 cm² contact area using a gelatine sponge swab moistened with saltwater-peptone solution.
3. Swab the stainless steel sheets horizontally from left to right covering the 24 cm² contact area using a dry gelatine sponge swab.
4. Swap the stainless steel sheets vertically from top to bottom covering the 24 cm² contact area using a dry gelatine sponge swab.
5. Place the swabs in stomacher bags.
6. Add the digesting solution to each stomacher bag.
7. Homogenize the stomacher bags using a stomacher.
8. Incubate the stomacher bags at 36° C. until the swabs have been dissolved.
9. Extraction of the spores is carried out using membrane filtration.

Example 6

Swabbing by Count-Tact Applicator

Introduction. The Count-Tact applicator standardizes surface testing, by applying a uniform pressure of 500±50 g for 10±1 seconds (draft European Standard: CEN/TC 243).
Description. The applicator is composed of two plastic elements:
 the base, which holds the Count-Tact plate in position, consisting of a push-button device mounted on a calibrated spring;
 a unit clipped onto the base, containing the electronic timer, the audible beep mechanism and batteries.
The method involves the following steps:
1. Slide the Count-Tact plate into position (lid facing outwards) under the two transparent clips fixed on the bottom of the base.
2. Remove the lid from the Count-Tact plate.
3. Hold the applicator in position against the surface where the sample is to be taken, without moving it (check that the surface is not damp).
4. After 10 seconds of contact with the surface, the audible beep will sound. Remove the applicator from the surface. Place the lid back on the plate, and remove the plate from the applicator (do not forget to clean the surface where the sample was taken in order to remove any possible traces of agar).
5. For incubation of the plates, refer to the Count-Tact technical sheet and the Count-Tact irradiated sheet.

Example 7

Validation Protocol from Polished Stainless Steel

Introduction. This protocol describes the validation of a method that is used for the microbiological sampling from polished stainless steel, which has been cleaned with isopropanol 70%.
The validation protocol is carried out in order to define the accuracy and precision of the method, and the recovery yield of micro-organisms from the type of material used in this test, using the described method of sampling.
This current test does apply whenever microbiological sampling from polished stainless steel cleaned with isopropanol is carried out in accordance with the current described sampling procedures.
Validation Parameters.
Selectivity
 Bacillus spores are used as markers of microbiological activity on the stainless steel. Because the spores are incubated at 55° C., it is considered unlikely that any microbiological contamination will influence the results during the validation test. Thus, selectivity is not relevant for this test.
Precision (Repeatability) and Accuracy (Recovery)
 Assessed by replicate extraction and analysis of swab samples using the same analyst, same equipment and same reagents within the same day, using
 2 concentration levels (5 and 25 spores); 1 surface material; 2 wipings of each surface material (pooled to one sample for analysis); Total of six replicates (n=6); Therefore, a total of 12 samples are analyzed.
Linearity
 Established using a three-point calibration curve, covering ranges from 5 to 50 spores. Test is carried out in six replicates, using three concentration levels (5, 25 and 50 spores), and 2 wipings of each surface material, pooled for analysis.
Intermediate Precision
 Established by replicate analysis on different days, using same reagent batches, same equipment, different analysts. Demonstrated using 2 concentration levels, 5 and 25 spores, 1 surface material and two wipings (pooled for analysis), and six replicates by three analysts on three days. Therefore, a total of 108 samples.
Equipment.
 Incubators, autoclave, sterile Drigalski spates, sterile gloves, gelatine swabs, mixer, membrane filtration equipment, colony counter, sterile stomacher bags.
Materials.
 Spore suspension (1*10⁶ spores/0.1 mL ethanol) of *Bacillus stearothermophilus* spores in 40% ethanol. Test samples of surface material (polished stainless steel). Template for swabbing area (6×4 cm=24 cm²)
Tryptic Soy Agar
Sterile Filter
Sterile 50 mL syringe Disposable sterile pipette tips
Count-Tact applicator with contact plates containing TSA, Tween and Lecithin.
Chemicals
Saltwater-peptone solution
Ethanol 96%
Elga water
Alcalase solution
Preparation of Test Validation Solutions
Positive control Class A: Spore suspensions containing 5 spores/313 µL is used as positive control. 0,100 ml spore suspension (1,6*10$^6$ spores/0,1 ml) is diluted in 9,90 ml 40% ethanol 3 times to give 1,6 spores/0,1ml in the final suspension, which corresponds to 5 spores/1,6 spores=3,125×0,1ml=0,3125 ml spore suspension to each contact sheet (24 cm$^2$).

Class B: Spore suspensions containing 25 spores/63µL is used as positive control. 0,100 ml spore suspension (1,6*10$^6$ spores/0,1 ml) is diluted in 19,90 ml 40% ethanol 2 times to give 40 spores/0,1 ml in the final suspension, which corresponds to 25 spores/40 spores=0,625×0,1 ml=0,0625 ml spore suspension to each contact sheet (24 cm$^2$).

Negative control
Sterile ethanol is used as negative control
Linearity

Three spore suspensions a) containing 5 spores, b) containing 25 spores and c) containing 50 spores will be used for the linearity study.

a) 0,100ml spore suspension (1,6*10$^6$ spores/0,1 ml) is diluted in 9,90 ml 40% ethanol 3 times to give 1,6 spores/0,1 ml in the final suspension, which corresponds to 5 spores/1,6 spores=3,125×0,1 ml=0,3125 ml spore suspension to each contact sheet (24 cm$^2$).

b) 0,100 ml spore suspension (1,6*10$^6$ spores/0,1 ml) Is diluted in 19,90 ml 40% ethanol 2 times to give 40 spores/0,1 ml in the final suspension, which corresponds to 25 spores/40 spores=0,625×0,1 ml=0,0625 ml spore suspension to each contact sheet (24 cm$^2$).

c) 0,100 ml spore suspension (1,6*10$^6$ spores/0,1 ml) is diluted in 19,90 ml 40% ethanol 2 times to give 40 spores/0,1 ml in the final suspension, which corresponds to 50 spores/40 spores=1,25×0,1 ml=0,125 ml spore suspension to each contact sheet (24 cm$^2$).

Sample Preparation.
Sampling Using Swab Technique.
  Spore suspension is applied to each stainless steel sheet
  Ethanol from the spore suspension on the stainless steel sheets is allowed to evaporate
  1,0 ml alcalase solution is diluted in 90 ml saltwater peptone solution.
  put stomacher bag in matching stomacher bag clip
  swab the stainless steel sheets horizontally from left to right covering the 24 cm$^2$ contact area using a swab moistened with slatwater-perpone solution.
  swab the stainless steel sheets horizontally from top to bottom covering the 24 cm$^2$ contact area using a swab moistened with slatwater-perpone solution.
  swab the stainless steel sheets horizontally from left to right covering the 24 cm$^2$ contact area using a dry swab.
  swab the stainless steel sheets horizontally from top to bottom covering the 24 cm$^2$ contact area using a dry swab.
  place the swabs in stomacher bags.
  add the diluted alcalase solution to each stomacher bag.
  homogenize the stomacher bags using a stomacher.
  incubate the stomacher bags at 36C. until the swabs have been dissolved (for at least 1 hour and maximum 2,5 hours).
  extraction of the spores is carried out using membrane filtration Sampling Using Count-Tact Applicator
  use gloves
  spore suspension is applied to each stainless steel sheet
  ethanol from the spore suspension on the stainless steel sheets is allowed to evaporate
  Count-Tact applicator is used on the stainless steel plates
  Negative controls are also added to the stainless steel sheets. Positive control samples are not added to stainless steel sheets, but are added directly to the Count-Tact application plates.

Incubation
  All samples are incubated at 55C.±2C. for at least 1 day to a maximum of 7 days.

Cleaning of Surface Material and Templates.
  Surface material and templates should be cleaned after each use and re-use:
  rinse the surface by wiping with laboratory paper that has been soaked in ethanol
  sterilization by autoclave at 121C. for not less than 20 minutes Calculations
Recovery %=sample (CFU)*100/added spores, where
sample=number of spores from Accuracy Test Solutions and
Added=number of spores in Accuracy Control Samples Validation Procedures
Recovery/Precision/Accuracy
  Recovery/Precision and Accuracy is investigated using stainless steel and performed in accordance with the methods outlined above. This test will be used for the calculation of the microbiological recovery from the test samples. Batches of reagents and equipment will not be altered since the change in these parameters is estimated to have little or no influence on the final test results.

Procedure
  One analyst will contaminate six stainless steel plates with approx. 5 and 25 *bacillus* spores each.
  Each stainless steel sheet is swabbed quadruplicate or sampled using the Count-Tact applicator
  The samples are incubated at 55±2C. for at least 1 day to a maximum of 7 days and counted.
  The tests will be carried out in accordance with the method described above.

Recovery/Accuracy
  Recovery should be higher than 20% compared to positive controls.
  The lowest recovery sets the limit (the lowest averag recovery at any given spore concentration −5 to 25 spores/24 cm$^2$).

Precision
  calculate mean and % RSD on replicate analysis
  % RSD should be less than 10%

Linearity
Procedure
  Prepare six identical samples using the spore suspensions a), b) and c) defined above. The samples will be used to establish recovery efficiencies for these levels of spores and used for the subsequent linear regression.

Evaluation
  recovery will be calculated for each level of spores and regression will be made from 5 to 50 spores.
  calculate the regression parameters of the standard curves and report slope, intercept and correlation coefficient of each curve.

the correlation coefficient should meet the criterial of $r^2>0,940$.

Intermediate precision
Procedure
  Same as for precision described above on three following days, using three different analysts.
Evaluation
  calculate recovery of spores
  calculate mean and % RSD on replicate analysis for each day
  calculate mean and % RSD using all days (intermediate precision day 1, day 2 and day 3)
  % RSD should be less than 15%

Example 8

Validation of Sampling from Polished Stainless Steel

Purpose
  To validate the methods used for microbiological sampling from polished stainless steel that has been cleaned with 70% isopropanol, referring to the validation protocol of Example 7.
Introduction.
  The validation study is carried out in order to define the accuracy, precision and linearity of methods used for microbiological sampling from surfaces and to estimate the recovery efficiency of micro-organisms from the type of material used in the test, using the described methods of sampling. In the present study the sampling was performed from polished stainless steel cleaned with 70% isopropanol. The rationale for sampling is that this is a common material used for equiment production. The method tested were sampling by swab technique and sampling by count-tact technique. The sampling was carried out on surfaces with an applied number of bacterial spores equal to the USP, NF guideline of class 10,000 production equipment and the EU-GMP guideline for microbiological purity of class 10,000 production equipment.
Results
Recovery
  Calculation of the recovery using the swab technique (Table 1) showed variations between analysts when applying 5 spores (40% to 175%) and variations when applying 25 spores (73% to 105%). The average recovery for all analysts using the swab technique were calculated to 80% when applying 5 spores and 91% when applying 25 spores.
  Calculation of recovery using the count-tact technique (Table 2) showed variations between analysts when applying 5 spores (54% to 88%) and variations when applying 25 spores (36% to 57%). The average recovery for all analysts using the count-tact technique were calculated to 74% when applying 5 spores and 45% when applying 25 spores.
Precision
  Calculations of relative standard deviation in percent (RSD %), when using the swab technique (Table 1) showed variations between analysts (34% to 70%) when applying 5 spores and variation (30% to 57%) when applying 25 spores. Using the count-tact technique (Table 2) RSD% was between 41% and 90% when applying 5 spores and between 20% and 65% when applying 25 spores.
Intermediate Precision
  Intermediate precision using the swab technique (Table 1) was 64% when applying 5 spores and 43% when applying 25 spores. Intermediate precision using the coun-tact technique (Table 2) was 77% when applying 5 spores and 54% when applying 25 spores.

TABLE 1

Sampling results using the swab technique

| Spores applied (calculated, not actual)[1] | | Assay (spores/24 cm$^2$) | | |
|---|---|---|---|---|
| | | 5 | 25 | 50 |
| Mean (cfu/24 cm$^2$) | Analyst 1[3] | 5 | 21 | [2] |
| Precision (RSD %) | | 42 | 57 | |
| Recovery (%) | | 175 | 105 | |
| Mean (cfu/24 cm$^2$) | Analyst 2[3] | 3 | 15 | [2] |
| Precision (RSD %) | | 70 | 30 | |
| Recovery (%) | | 59 | 73 | |
| Mean (cfu/24 cm$^2$) | Analyst 3[3] | 2 | 17 | 29 |
| Precision (RSD %) | | 34 | 32 | 39 |
| Recovery (%) | | 40 | 94 | 95 |
| Mean (cfu/24 cm$^2$) | Analyst 1, 2, 3 | 3 | 18 | [2] |
| Precision (RSD %) | | 64 | 43 | |
| Recovery (%) | | 80 | 91 | |

[1] The number of spores applied was calculated to be 5, 25 or 50. The actual amound of spores applied was used for calculating recoveries.
[2] One analyst only carried out sampling from surfaces with 50 spores applied by the sole purpose of investigating linearity
[3] Each analyst completed the sampling and analysis in six replicates.

Linearity from 5 to 50 spores:
Correlation coefficient (R)=0,9995; $R^2$=0,9990; Intercept=−2,3; Slope=1,0
Linearity
  Linearity was calculated by regression between applied spore concentrations of 5, 25 and 50 spores by one analyst. The defined level of acceptance was a $R^2$>0,9400. The calculated $R^2$ was 0,9990 when using the swab technique and 0,9989 when using the count-tact technique.

TABLE 2

Sampling results using the count-tact technique

| Spores applied (calculated, not actual)[1] | | Assay (spores/24 cm$^2$) | | |
|---|---|---|---|---|
| | | 5 | 25 | 50 |
| Mean (cfu/24 cm$^2$) | Analyst 1[3] | 4 | 14 | 20 |
| Precision (RSD %) | | 70 | 20 | 24 |
| Recovery (%) | | 88 | 45 | 40 |
| Mean (cfu/24 cm$^2$) | Analyst 2[3] | 2 | 7 | [2] |
| Precision (RSD %) | | 41 | 44 | |
| Recovery (%) | | 79 | 36 | |
| Mean (cfu/24 cm$^2$) | Analyst 3[3] | 2 | 13 | [2] |
| Precision (RSD %) | | 90 | 65 | |
| Recovery (%) | | 54 | 57 | |
| Mean (cfu/24 cm$^2$) | Analyst 1, 2, 3 | 3 | 11 | [2] |
| Precision (RSD %) | | 77 | 54 | |
| Recovery (%) | | 74 | 45 | |

[1] The number of spores applied was calculated to be 5, 25 or 50. The actual amound of spores applied was used for calculating recoveries.
[2] One analyst only carried out sampling from surfaces with 50 spores applied by the sole purpose of investigating linearity
[3] Each analyst completed the sampling and analysis in six replicates.

Linearity from 5 to 50 spores:
Correlation coefficient (R)=0,9989; $R^2$=0,9979; Intercept=−2,4; Slope=0,4
Discussion
Recovery
  The level of recovery of microorganisms from surfaces is critical when complying with USP/NF guidelines and EU-GMP guidelines. The bacterial recovery using both the swab technique and the count-tact technique as described in the protocol was better than anticipated when recovering micro-organisms from the samples with a known microbiological contamination rqual to the USP/NF guideline and the EU-GMP guideline. The average (for all analysts) lowest recovery was 80% for the swab technique and 45% for the count-tact technique. For the chosen sampling method used on stainless steel this recovery should be used to estimate the actual amount of microorganism on the surface.

Precision

The relative standard deviation (% RSD) on replicate analysis (for a single analyst) was larger than first anticipated. The comparison of the % RSD for the positive controls and the assay however showed that high % RSD is mainly caused by the analysis of the samples and not by the use of count-tact or swab technique. It should have been expected not to achieve a % RSD corresponding to chemical analysis, since it is generally known that % RSD is much larger for microbiological analysis than chemical analysis.

Intermediate Precision

The relative standard deviation (% RSD) on replicate analysis (between analysts) was larger than first anticipated. The comparison of the % RSD for the positive controls and the assay however showed that the high % RSD is mainly caused by the analysis of the samples and not by the swab or count-tact techniques used. It should have been expected not to achieve a % RSD corresponding to chemical analysis, since it is generally known that % RSD Is much larger for microbiological analysis than chemical analysis.

The average % RSD calculated for the lowest recoveries given above was 64% for the swab technique and 54% for the count-tact method. To correct for the large variations on the analysis the % RSD should be taken into account when estimating the actual number of microorganisms on a surface.

Conclusions

The results show that the methods described above can be used for sampling of microorganisms from polished stainless steel in an overall satisfactory way and show no reason not to expect the method to be amenable to all surfaces. The level of recovery of micro-organisms from surfaces is critical when complying with USP/NF guidelines and EU-GMP guidelines. The bacterial recovery using both the swab technique and he count-tact applicator as described in the protocol was better than anticipated when recovering micro-organisms from samples with a known microbiological contamination equal to the USP/NF guideline and the EU-GMP guideline.

The invention claimed is:

1. A single-use device for sampling and recovering a target, said device comprising a sterile swab and a handle attached to said swab, wherein said swab is a gelatine-based sponge, and wherein said device is contained in a sealed package.

2. The device according to claim 1, wherein the gelatine-based sponge has a water absorption capacity of at least 30 g/g as determined by USP method "Absorbable Gelatine Sponge: Water Absorption".

3. A kit comprising:
   i) a swab and a handle attached to said swab, wherein said swab is a gelatine-based sponge; and
   ii) a neutral diluent selected from the group consisting of saline, saline peptone, buffered saline peptone, Ringer solution and an organic and inorganic buffer.

4. A method for collecting a target from a collection medium comprising:
   i) providing a device according to claim 1;
   ii) making contact between the swab of the device according to claim 1 and the target to transfer said target from the collection medium to the swab of the device; and
   iii) transferring said target from the swab of said device to a transfer medium to thereby recover said target from said collection medium.

5. A method for sampling an area for a target comprising:
   i) swiping the surface of the area with a first gelatine-based sponge pre-wetted with a neutral diluent or dispersing agent; followed by
   ii) swiping said surface with a dry second gelatine-based sponge; and
   iii) transferring said target from said first and second sponges to a transfer medium. thereby recovering the target from said surface.

6. A method of lowering the amount of a target in a sample area comprising:
   (i) providing a device according to claim 1,
   (ii) making contact between the swab of the device according to claim 1 and at least a portion of said sample area, so that an amount of the target adheres to the swab of the device, and
   (iii) transferring the adhered target from the swab of said device to a transfer medium.

7. The method according to any one of claims 4, 5 and 6, wherein the target is selected from the group consisting of a virus, a microorganism, a mammalian cell and an organic molecule.

8. The method according to claim 7, wherein the organic molecule is selected from the group consisting of a nucleotide, a nucleic acid, a protein and a detergent.

9. The method according to any one of claims 4, 5 and 6 wherein said transferring step includes digestion of said gelatine swab.

10. The method according to any one of claims 4, 5 and 6 wherein said transferring step includes washing said target from the gelatine swab.

11. The method according to claim 9, wherein the digestion comprises addition of an agent selected from the group consisting of an enzyme, a mineral acid, a carboxylic acid, a base and combinations thereof.

12. The method according to claim 9, further comprising extraction of the target by membrane filtration.

13. The method of claim 6, wherein the micro-organism is selected from the group consisting of bacteria, bacterial spores, archea, yeast and fungi.

14. The method of claim 6, wherein the mammalian cell is a cell from blood plasma.

15. The method of claim 14, wherein the mammalian cell is selected from the group consisting of leukocytes, erythrocytes and thrombocytes.

16. The device according to claim 1, wherein said handle comprises a material selected from the group consisting of wood, natural or synthetic polymeric material, plastics, and rubber materials.

17. A method for sampling an area for a target comprising:
   i) a wet-sampling step comprising swiping the surface of the area with the gelatine-based sponge of a first device according to claim 1, wherein said gelatine-based sponge is pre-wetted;
   ii) followed by a dry-sampling step comprising swiping said surface with the gelatine-based sponge of a second device according to claim 1,
   iii) transferring target collected by said wet-sampling and dry-sampling steps to a transfer medium, thereby recovering the target from said surface.

18. The method according to claim 17, wherein said handle comprises a material selected from the group consisting of wood, natural or synthetic polymeric material, plastics, and rubber materials.

19. The method according to any one of claims 4 and 6 wherein said swab is pre-wetted.

20. The method according to any one of claims 4, 5 and 6, wherein said target comprises cells and wherein said method further comprises culturing cells collected on the swab in a growth medium.

* * * * *